US008773761B2

(12) United States Patent
Sataka et al.

(10) Patent No.: US 8,773,761 B2
(45) Date of Patent: Jul. 8, 2014

(54) OPTICAL MEMBER AND MICROSCOPE

(71) Applicant: Nikon Corporation, Tokyo (JP)

(72) Inventors: Ryoichi Sataka, Yokohama (JP); Mayumi Hagiwara, Atsugi (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 13/728,102

(22) Filed: Dec. 27, 2012

(65) Prior Publication Data

US 2013/0135716 A1    May 30, 2013

Related U.S. Application Data

(63) Continuation of application No. PCT/JP2011/065214, filed on Jul. 1, 2011.

(30) Foreign Application Priority Data

Jul. 1, 2010    (JP) ................................ 2010-151104

(51) Int. Cl.
G02B 21/06 (2006.01)
(52) U.S. Cl.
USPC .......................................................... 359/385
(58) Field of Classification Search
USPC .......................................... 359/385, 387, 388
See application file for complete search history.

(56) References Cited

U.S. PATENT DOCUMENTS

| 6,094,300 | A | 7/2000 | Kashima et al. | |
|---|---|---|---|---|
| 7,675,676 | B2 * | 3/2010 | Nakata | 359/389 |
| 8,270,088 | B2 * | 9/2012 | Yokoi | 359/637 |
| 2008/0290293 | A1 | 11/2008 | Motomura | |
| 2009/0009761 | A1 | 1/2009 | Yamazaki et al. | |
| 2009/0147256 | A1 | 6/2009 | Okugawa | |
| 2010/0067102 | A1 * | 3/2010 | Yokoi et al. | 359/385 |
| 2011/0043906 | A1 * | 2/2011 | Saito et al. | 359/385 |

FOREIGN PATENT DOCUMENTS

| JP | A-5-232314 | 9/1993 |
|---|---|---|
| JP | U-06-72114 | 10/1994 |
| JP | A-9-101110 | 4/1997 |
| JP | A-10-153705 | 6/1998 |
| JP | A-10-206742 | 8/1998 |
| JP | A-2006-106346 | 4/2006 |
| JP | A-2007-78773 | 3/2007 |
| JP | A-2008-276191 | 11/2008 |

(Continued)

OTHER PUBLICATIONS

International Search Report issued in International Patent Application No. PCT/JP2011/065214 dated Sep. 6, 2011.

*Primary Examiner* — Frank Font
(74) *Attorney, Agent, or Firm* — Oliff PLC

(57) ABSTRACT

An optical member and a microscope that allow acquiring brighter and sharper images when fluorescent observation is performed while stimulating a sample with light. Illumination light from a laser unit is split into stimulation light and excitation light by a dichroic mirror. In other words, half of the illumination light is transmitted through the dichroic mirror and becomes the stimulation light, and half of the illumination light is reflected by the dichroic mirror and becomes the excitation light. Half of the excitation light is reflected by a dichroic mirror and is irradiated onto a sample, and half of the stimulation light transmits through the dichroic mirror and is irradiated onto the sample. Fluorescence generated from the sample is totally reflected by the dichroic mirror and the dichroic mirror, and is received by a photodetector.

9 Claims, 13 Drawing Sheets

(56) References Cited

FOREIGN PATENT DOCUMENTS

| JP | A-2009-8554 | 1/2009 |
| JP | A-2009-238990 | 10/2009 |
| WO | WO 2008/004336 A1 | 1/2008 |

* cited by examiner

FIG. 2A

| LAYER NUMBER | SUBSTANCE | FILM THICKNESS (nm) | LAYER NUMBER | SUBSTANCE | FILM THICKNESS (nm) | LAYER NUMBER | SUBSTANCE | FILM THICKNESS (nm) |
|---|---|---|---|---|---|---|---|---|
| 1 | Nb2O5 | 37.33 | 61 | Nb2O5 | 112.46 | 121 | Nb2O5 | 85.48 |
| 2 | SiO2 | 10.00 | 62 | SiO2 | 140.02 | 122 | SiO2 | 58.96 |
| 3 | Nb2O5 | 45.08 | 63 | Nb2O5 | 68.80 | 123 | Nb2O5 | 81.75 |
| 4 | SiO2 | 98.44 | 64 | SiO2 | 162.81 | 124 | SiO2 | 68.13 |
| 5 | Nb2O5 | 97.13 | 65 | Nb2O5 | 130.64 | 125 | Nb2O5 | 79.59 |
| 6 | SiO2 | 119.07 | 66 | SiO2 | 15.25 | 126 | SiO2 | 110.50 |
| 7 | Nb2O5 | 96.63 | 67 | Nb2O5 | 60.28 | 127 | Nb2O5 | 53.91 |
| 8 | SiO2 | 117.86 | 68 | SiO2 | 74.03 | 128 | SiO2 | 81.31 |
| 9 | Nb2O5 | 105.92 | 69 | Nb2O5 | 82.61 | 129 | Nb2O5 | 128.20 |
| 10 | SiO2 | 82.58 | 70 | SiO2 | 99.75 | 130 | SiO2 | 31.99 |
| 11 | Nb2O5 | 110.25 | 71 | Nb2O5 | 92.90 | 131 | Nb2O5 | 21.03 |
| 12 | SiO2 | 88.82 | 72 | SiO2 | 67.25 | 132 | SiO2 | 71.76 |
| 13 | Nb2O5 | 98.62 | 73 | Nb2O5 | 120.64 | 133 | Nb2O5 | 50.49 |
| 14 | SiO2 | 91.30 | 74 | SiO2 | 57.50 | 134 | SiO2 | 105.23 |
| 15 | Nb2O5 | 81.32 | 75 | Nb2O5 | 43.09 | 135 | Nb2O5 | 69.80 |
| 16 | SiO2 | 47.09 | 76 | SiO2 | 34.83 | 136 | SiO2 | 93.44 |
| 17 | Nb2O5 | 102.35 | 77 | Nb2O5 | 134.63 | 137 | Nb2O5 | 168.18 |
| 18 | SiO2 | 118.02 | 78 | SiO2 | 74.67 | 138 | SiO2 | 52.96 |
| 19 | Nb2O5 | 87.67 | 79 | Nb2O5 | 94.53 | 139 | Nb2O5 | 82.63 |
| 20 | SiO2 | 121.28 | 80 | SiO2 | 101.84 | 140 | SiO2 | 62.89 |

FIG. 2B

| | | | | | | | | |
|---|---|---|---|---|---|---|---|---|
| 21 | Nb2O5 | 135.15 | 81 | Nb2O5 | 63.96 | 141 | Nb2O5 | 88.00 |
| 22 | SiO2 | 107.75 | 82 | SiO2 | 77.38 | 142 | SiO2 | 208.33 |
| 23 | Nb2O5 | 97.78 | 83 | Nb2O5 | 89.55 | 143 | Nb2O5 | 164.72 |
| 24 | SiO2 | 46.73 | 84 | SiO2 | 125.57 | 144 | SiO2 | 66.68 |
| 25 | Nb2O5 | 132.16 | 85 | Nb2O5 | 90.96 | 145 | Nb2O5 | 82.26 |
| 26 | SiO2 | 122.12 | 86 | SiO2 | 113.94 | 146 | SiO2 | 92.66 |
| 27 | Nb2O5 | 85.00 | 87 | Nb2O5 | 178.15 | 147 | Nb2O5 | 265.43 |
| 28 | SiO2 | 160.78 | 88 | SiO2 | 89.06 | 148 | SiO2 | 62.96 |
| 29 | Nb2O5 | 86.02 | 89 | Nb2O5 | 103.37 | 149 | Nb2O5 | 43.41 |
| 30 | SiO2 | 91.68 | 90 | SiO2 | 83.92 | 150 | SiO2 | 39.95 |
| 31 | Nb2O5 | 97.25 | 91 | Nb2O5 | 100.93 | 151 | Nb2O5 | 36.53 |
| 32 | SiO2 | 32.88 | 92 | SiO2 | 75.08 | 152 | SiO2 | 40.86 |
| 33 | Nb2O5 | 182.56 | 93 | Nb2O5 | 77.94 | 153 | Nb2O5 | 43.08 |
| 34 | SiO2 | 26.34 | 94 | SiO2 | 81.08 | 154 | SiO2 | 42.87 |
| 35 | Nb2O5 | 109.01 | 95 | Nb2O5 | 84.45 | 155 | Nb2O5 | 74.09 |
| 36 | SiO2 | 100.19 | 96 | SiO2 | 110.55 | 156 | SiO2 | 207.47 |
| 37 | Nb2O5 | 103.16 | 97 | Nb2O5 | 323.51 | 157 | Nb2O5 | 141.53 |
| 38 | SiO2 | 114.33 | 98 | SiO2 | 93.75 | 158 | SiO2 | 41.36 |
| 39 | Nb2O5 | 103.19 | 99 | Nb2O5 | 78.83 | 159 | Nb2O5 | 29.46 |
| 40 | SiO2 | 73.58 | 100 | SiO2 | 43.47 | 160 | SiO2 | 38.07 |

FIG. 2C

| 41 | Nb2O5 | 134.70 | 101 | Nb2O5 | 84.55 | 161 | Nb2O5 | 44.46 |
|---|---|---|---|---|---|---|---|---|
| 42 | SiO2 | 33.69 | 102 | SiO2 | 98.80 | 162 | SiO2 | 209.49 |
| 43 | Nb2O5 | 122.79 | 103 | Nb2O5 | 64.45 | 163 | Nb2O5 | 60.06 |
| 44 | SiO2 | 126.25 | 104 | SiO2 | 77.94 | 164 | SiO2 | 23.04 |
| 45 | Nb2O5 | 77.70 | 105 | Nb2O5 | 60.74 | 165 | Nb2O5 | 19.69 |
| 46 | SiO2 | 140.18 | 106 | SiO2 | 42.11 | 166 | SiO2 | 55.37 |
| 47 | Nb2O5 | 122.85 | 107 | Nb2O5 | 88.55 | 167 | Nb2O5 | 562.61 |
| 48 | SiO2 | 105.01 | 108 | SiO2 | 73.57 | 168 | SiO2 | 10.35 |
| 49 | Nb2O5 | 33.23 | 109 | Nb2O5 | 75.88 | 169 | Nb2O5 | 11.65 |
| 50 | SiO2 | 10.00 | 110 | SiO2 | 96.56 | 170 | SiO2 | 115.68 |
| 51 | Nb2O5 | 31.96 | 111 | Nb2O5 | 56.82 | 171 | Nb2O5 | 193.44 |
| 52 | SiO2 | 110.47 | 112 | SiO2 | 91.92 | 172 | SiO2 | 41.39 |
| 53 | Nb2O5 | 69.16 | 113 | Nb2O5 | 41.63 | 173 | Nb2O5 | 14.15 |
| 54 | SiO2 | 138.73 | 114 | SiO2 | 22.33 | 174 | SiO2 | 110.99 |
| 55 | Nb2O5 | 282.06 | 115 | Nb2O5 | 30.00 | 175 | Nb2O5 | 63.49 |
| 56 | SiO2 | 71.28 | 116 | SiO2 | 58.91 | 176 | SiO2 | 70.81 |
| 57 | Nb2O5 | 198.55 | 117 | Nb2O5 | 64.23 | 177 | | |
| 58 | SiO2 | 72.83 | 118 | SiO2 | 45.82 | 178 | | |
| 59 | Nb2O5 | 94.16 | 119 | Nb2O5 | 119.26 | 179 | | |
| 60 | SiO2 | 143.03 | 120 | SiO2 | 21.34 | 180 | | |

FIG. 4A

| LAYER NUMBER | SUBSTANCE | FILM THICKNESS (nm) | LAYER NUMBER | SUBSTANCE | FILM THICKNESS (nm) | LAYER NUMBER | SUBSTANCE | FILM THICKNESS (nm) |
|---|---|---|---|---|---|---|---|---|
| 1 | Nb2O5 | 92.57 | 61 | Nb2O5 | 16.90 | 121 | | |
| 2 | SiO2 | 35.84 | 62 | SiO2 | 124.46 | 122 | | |
| 3 | Nb2O5 | 232.13 | 63 | Nb2O5 | 14.67 | 123 | | |
| 4 | SiO2 | 10.76 | 64 | SiO2 | 49.37 | 124 | | |
| 5 | Nb2O5 | 96.42 | 65 | Nb2O5 | 20.04 | 125 | | |
| 6 | SiO2 | 61.99 | 66 | SiO2 | 85.27 | 126 | | |
| 7 | Nb2O5 | 165.72 | 67 | Nb2O5 | 76.85 | 127 | | |
| 8 | SiO2 | 80.19 | 68 | SiO2 | 106.48 | 128 | | |
| 9 | Nb2O5 | 235.56 | 69 | Nb2O5 | 62.60 | 129 | | |
| 10 | SiO2 | 19.06 | 70 | SiO2 | 135.70 | 130 | | |
| 11 | Nb2O5 | 181.02 | 71 | Nb2O5 | 61.47 | 131 | | |
| 12 | SiO2 | 74.35 | 72 | SiO2 | 126.49 | 132 | | |
| 13 | Nb2O5 | 81.75 | 73 | Nb2O5 | 45.96 | 133 | | |
| 14 | SiO2 | 47.46 | 74 | SiO2 | 134.24 | 134 | | |
| 15 | Nb2O5 | 91.33 | 75 | Nb2O5 | 53.85 | 135 | | |
| 16 | SiO2 | 55.83 | 76 | SiO2 | 148.31 | 136 | | |
| 17 | Nb2O5 | 228.26 | 77 | Nb2O5 | 58.76 | 137 | | |
| 18 | SiO2 | 36.13 | 78 | SiO2 | 116.73 | 138 | | |
| 19 | Nb2O5 | 175.93 | 79 | Nb2O5 | 56.49 | 139 | | |
| 20 | SiO2 | 66.61 | 80 | SiO2 | 134.25 | 140 | | |

FIG. 4B

| 21 | Nb2O5 | 69.26 | 81 | Nb2O5 | 33.00 | 141 | | | |
|---|---|---|---|---|---|---|---|---|---|
| 22 | SiO2 | 88.54 | 82 | SiO2 | 183.16 | 142 | | | |
| 23 | Nb2O5 | 111.18 | 83 | Nb2O5 | 26.51 | 143 | | | |
| 24 | SiO2 | 15.85 | 84 | SiO2 | 168.26 | 144 | | | |
| 25 | Nb2O5 | 211.89 | 85 | Nb2O5 | 29.71 | 145 | | | |
| 26 | SiO2 | 28.40 | 86 | SiO2 | 131.01 | 146 | | | |
| 27 | Nb2O5 | 82.16 | 87 | Nb2O5 | 61.16 | 147 | | | |
| 28 | SiO2 | 50.98 | 88 | SiO2 | 106.87 | 148 | | | |
| 29 | Nb2O5 | 89.00 | 89 | Nb2O5 | 73.35 | 149 | | | |
| 30 | SiO2 | 236.36 | 90 | SiO2 | 113.90 | 150 | | | |
| 31 | Nb2O5 | 115.08 | 91 | Nb2O5 | 69.74 | 151 | | | |
| 32 | SiO2 | 174.24 | 92 | SiO2 | 121.64 | 152 | | | |
| 33 | Nb2O5 | 104.31 | 93 | Nb2O5 | 63.18 | 153 | | | |
| 34 | SiO2 | 68.64 | 94 | SiO2 | 127.74 | 154 | | | |
| 35 | Nb2O5 | 75.43 | 95 | Nb2O5 | 38.44 | 155 | | | |
| 36 | SiO2 | 427.73 | 96 | SiO2 | 152.85 | 156 | | | |
| 37 | Nb2O5 | 17.14 | 97 | Nb2O5 | 39.25 | 157 | | | |
| 38 | SiO2 | 167.01 | 98 | SiO2 | 84.81 | 158 | | | |
| 39 | Nb2O5 | 106.26 | 99 | Nb2O5 | 38.69 | 159 | | | |
| 40 | SiO2 | 48.21 | 100 | SiO2 | 26.19 | 160 | | | |

FIG. 4C

| 41 | Nb2O5 | 60.37  | 101 | Nb2O5 | 23.08 | 161 |
| 42 | SiO2  | 141.04 | 102 | SiO2  | 75.40 | 162 |
| 43 | Nb2O5 | 58.51  | 103 | Nb2O5 | 67.45 | 163 |
| 44 | SiO2  | 41.60  | 104 | SiO2  | 42.12 | 164 |
| 45 | Nb2O5 | 113.76 | 105 | Nb2O5 | 10.00 | 165 |
| 46 | SiO2  | 455.95 | 106 |       |       | 166 |
| 47 | Nb2O5 | 56.18  | 107 |       |       | 167 |
| 48 | SiO2  | 127.76 | 108 |       |       | 168 |
| 49 | Nb2O5 | 62.66  | 109 |       |       | 169 |
| 50 | SiO2  | 142.07 | 110 |       |       | 170 |
| 51 | Nb2O5 | 56.58  | 111 |       |       | 171 |
| 52 | SiO2  | 131.34 | 112 |       |       | 172 |
| 53 | Nb2O5 | 59.50  | 113 |       |       | 173 |
| 54 | SiO2  | 319.72 | 114 |       |       | 174 |
| 55 | Nb2O5 | 99.99  | 115 |       |       | 175 |
| 56 | SiO2  | 179.21 | 116 |       |       | 176 |
| 57 | Nb2O5 | 74.75  | 117 |       |       | 177 |
| 58 | SiO2  | 141.84 | 118 |       |       | 178 |
| 59 | Nb2O5 | 42.52  | 119 |       |       | 179 |
| 60 | SiO2  | 175.83 | 120 |       |       | 180 |

FIG. 6A

| LAYER NUMBER | SUBSTANCE | FILM THICKNESS (nm) | LAYER NUMBER | SUBSTANCE | FILM THICKNESS (nm) | LAYER NUMBER | SUBSTANCE | FILM THICKNESS (nm) | LAYER NUMBER | SUBSTANCE | FILM THICKNESS (nm) |
|---|---|---|---|---|---|---|---|---|---|---|---|
| 1 | Nb2O5 | 10.79 | 61 | Nb2O5 | 35.56 | 121 | Nb2O5 | 32.04 | 181 | Nb2O5 | 33.56 |
| 2 | SiO2 | 51.29 | 62 | SiO2 | 117.18 | 122 | SiO2 | 93.48 | 182 | SiO2 | 48.17 |
| 3 | Nb2O5 | 103.34 | 63 | Nb2O5 | 88.34 | 123 | Nb2O5 | 94.39 | 183 | Nb2O5 | 39.99 |
| 4 | SiO2 | 24.98 | 64 | SiO2 | 101.45 | 124 | SiO2 | 79.82 | 184 | SiO2 | 68.03 |
| 5 | Nb2O5 | 11.42 | 65 | Nb2O5 | 35.97 | 125 | Nb2O5 | 36.28 | 185 | Nb2O5 | 10.00 |
| 6 | SiO2 | 40.89 | 66 | SiO2 | 39.57 | 126 | SiO2 | 39.11 | 186 | | |
| 7 | Nb2O5 | 97.68 | 67 | Nb2O5 | 19.50 | 127 | Nb2O5 | 32.53 | 187 | | |
| 8 | SiO2 | 144.80 | 68 | SiO2 | 80.89 | 128 | SiO2 | 48.80 | 188 | | |
| 9 | Nb2O5 | 14.84 | 69 | Nb2O5 | 37.47 | 129 | Nb2O5 | 49.94 | 189 | | |
| 10 | SiO2 | 41.75 | 70 | SiO2 | 10.00 | 130 | SiO2 | 53.15 | 190 | | |
| 11 | Nb2O5 | 114.98 | 71 | Nb2O5 | 10.00 | 131 | Nb2O5 | 32.03 | 191 | | |
| 12 | SiO2 | 79.56 | 72 | SiO2 | 158.60 | 132 | SiO2 | 41.78 | 192 | | |
| 13 | Nb2O5 | 27.54 | 73 | Nb2O5 | 74.98 | 133 | Nb2O5 | 30.69 | 193 | | |
| 14 | SiO2 | 17.41 | 74 | SiO2 | 39.15 | 134 | SiO2 | 61.42 | 194 | | |
| 15 | Nb2O5 | 47.59 | 75 | Nb2O5 | 18.54 | 135 | Nb2O5 | 64.01 | 195 | | |
| 16 | SiO2 | 128.11 | 76 | SiO2 | 220.61 | 136 | SiO2 | 10.00 | 196 | | |
| 17 | Nb2O5 | 78.84 | 77 | Nb2O5 | 39.58 | 137 | Nb2O5 | 10.00 | 197 | | |
| 18 | SiO2 | 10.00 | 78 | SiO2 | 67.04 | 138 | SiO2 | 118.08 | 198 | | |
| 19 | Nb2O5 | 10.00 | 79 | Nb2O5 | 19.88 | 139 | Nb2O5 | 10.00 | 199 | | |
| 20 | SiO2 | 71.04 | 80 | SiO2 | 52.85 | 140 | SiO2 | 10.00 | 200 | | |

FIG. 6B

| | | | | | | |
|---|---|---|---|---|---|---|
| 21 | Nb2O5 | 10.00 | 81 | Nb2O5 | 37.13 | 141 | Nb2O5 | 85.21 |
| 22 | SiO2 | 172.82 | 82 | SiO2 | 79.27 | 142 | SiO2 | 10.00 |
| 23 | Nb2O5 | 79.75 | 83 | Nb2O5 | 10.00 | 143 | Nb2O5 | 59.98 |
| 24 | SiO2 | 116.94 | 84 | SiO2 | 10.00 | 144 | SiO2 | 46.37 |
| 25 | Nb2O5 | 71.78 | 85 | Nb2O5 | 90.02 | 145 | Nb2O5 | 20.52 |
| 26 | SiO2 | 114.76 | 86 | SiO2 | 76.11 | 146 | SiO2 | 49.32 |
| 27 | Nb2O5 | 76.76 | 87 | Nb2O5 | 39.49 | 147 | Nb2O5 | 104.35 |
| 28 | SiO2 | 101.05 | 88 | SiO2 | 39.70 | 148 | SiO2 | 24.48 |
| 29 | Nb2O5 | 10.01 | 89 | Nb2O5 | 31.92 | 149 | Nb2O5 | 10.00 |
| 30 | SiO2 | 20.46 | 90 | SiO2 | 49.68 | 150 | SiO2 | 88.40 |
| 31 | Nb2O5 | 86.71 | 91 | Nb2O5 | 53.63 | 151 | Nb2O5 | 74.48 |
| 32 | SiO2 | 19.85 | 92 | SiO2 | 30.13 | 152 | SiO2 | 11.83 |
| 33 | Nb2O5 | 204.28 | 93 | Nb2O5 | 61.01 | 153 | Nb2O5 | 10.00 |
| 34 | SiO2 | 160.68 | 94 | SiO2 | 25.35 | 154 | SiO2 | 113.95 |
| 35 | Nb2O5 | 63.15 | 95 | Nb2O5 | 31.26 | 155 | Nb2O5 | 32.14 |
| 36 | SiO2 | 140.18 | 96 | SiO2 | 38.19 | 156 | SiO2 | 38.94 |
| 37 | Nb2O5 | 55.36 | 97 | Nb2O5 | 76.93 | 157 | Nb2O5 | 29.96 |
| 38 | SiO2 | 140.62 | 98 | SiO2 | 67.92 | 158 | SiO2 | 50.91 |
| 39 | Nb2O5 | 61.25 | 99 | Nb2O5 | 29.08 | 159 | Nb2O5 | 44.25 |
| 40 | SiO2 | 66.23 | 100 | SiO2 | 30.50 | 160 | SiO2 | 54.87 |

FIG. 6C

| | | | | | | |
|---|---|---|---|---|---|---|
| 41 | Nb2O5 | 14.64 | 101 | Nb2O5 | 37.11 | 161 | Nb2O5 | 29.42 |
| 42 | SiO2 | 34.21 | 102 | SiO2 | 85.08 | 162 | SiO2 | 47.26 |
| 43 | Nb2O5 | 46.45 | 103 | Nb2O5 | 44.95 | 163 | Nb2O5 | 32.09 |
| 44 | SiO2 | 115.53 | 104 | SiO2 | 36.87 | 164 | SiO2 | 60.36 |
| 45 | Nb2O5 | 74.89 | 105 | Nb2O5 | 23.41 | 165 | Nb2O5 | 57.85 |
| 46 | SiO2 | 103.38 | 106 | SiO2 | 50.89 | 166 | SiO2 | 10.00 |
| 47 | Nb2O5 | 72.68 | 107 | Nb2O5 | 69.48 | 167 | Nb2O5 | 57.41 |
| 48 | SiO2 | 101.72 | 108 | SiO2 | 103.01 | 168 | SiO2 | 37.50 |
| 49 | Nb2O5 | 10.00 | 109 | Nb2O5 | 12.15 | 169 | Nb2O5 | 42.23 |
| 50 | SiO2 | 23.09 | 110 | SiO2 | 48.63 | 170 | SiO2 | 46.45 |
| 51 | Nb2O5 | 36.86 | 111 | Nb2O5 | 46.08 | 171 | Nb2O5 | 24.60 |
| 52 | SiO2 | 131.63 | 112 | SiO2 | 30.60 | 172 | SiO2 | 119.33 |
| 53 | Nb2O5 | 66.06 | 113 | Nb2O5 | 49.95 | 173 | Nb2O5 | 13.52 |
| 54 | SiO2 | 134.71 | 114 | SiO2 | 60.91 | 174 | SiO2 | 27.96 |
| 55 | Nb2O5 | 61.13 | 115 | Nb2O5 | 26.30 | 175 | Nb2O5 | 77.45 |
| 56 | SiO2 | 161.07 | 116 | SiO2 | 41.79 | 176 | SiO2 | 53.83 |
| 57 | Nb2O5 | 124.91 | 117 | Nb2O5 | 35.03 | 177 | Nb2O5 | 32.42 |
| 58 | SiO2 | 50.94 | 118 | SiO2 | 228.88 | 178 | SiO2 | 49.04 |
| 59 | Nb2O5 | 32.27 | 119 | Nb2O5 | 31.57 | 179 | Nb2O5 | 36.25 |
| 60 | SiO2 | 31.13 | 120 | SiO2 | 26.13 | 180 | SiO2 | 52.57 |

OPTICAL MEMBER AND MICROSCOPE

This is a Continuation of Application No. PCT/JP2011/065214 filed Jul. 1, 2011 which claims the benefit of Japanese Patent Application No. 2010-151104 filed Jul. 1, 2010 The disclosure of the prior applications is hereby incorporated by reference herein in their entirety.

TECHNICAL FIELD

The present invention relates to an optical member and a microscope that can acquire brighter and sharper observation images when fluorescent observation is performed while optically stimulating a sample.

BACKGROUND ART

A scanning microscope which acquires an observed image of an observation target sample by scanning the sample with an excitation light, while stimulating the sample with a stimulation light, has been available (e.g. see Patent Document 1 and Patent Document 2).

In many cases when fluorescent observation of a sample is performed using a stimulation light and an excitation light which have a same wavelength in this kind of scanning microscope, a laser beam emitted from a same light source is split into the stimulation light and the excitation light using a beam splitting half-mirror. In this case, the stimulation light and the excitation light are scanned by different scanners and then combined by a beam combining half-mirror, and are irradiated onto the sample.

If fluorescence is generated from the sample by the irradiation of the excitation light, this fluorescence is received by a photodetector via the beam combining half-mirror and the beam splitting half-mirror, and an observation image of the sample is generated based on the electric signals generated as a result. The user can observe the observation surface of the sample by viewing the observation image acquired like this.

Patent Document 1: WO 2008/004336
Patent Document 2: Japanese Patent Application Laid-Open No. 2007-78773

DISCLOSURE OF THE INVENTION

In the case of the above mentioned technique however, the fluorescence generated in the sample is reduced by half and is weakened each time it passes through the beam combining half-mirror and the beam splitting half-mirror. As a result, the photodetector cannot receive sufficient light quantity of fluorescence, and the observation image becomes dark and blurred.

With the foregoing in view, it is an object of the present invention to acquire brighter and sharper images when fluorescent observation is performed while stimulating the sample with light.

An optical member of the present invention reflects a part of first light having a first wavelength that has entered, and transmits the part of first light, whereby the first light is split at a predetermined ratio, and approximately all second light having a second wavelength that has entered is transmitted or reflected, with the second wavelength of the second light being different from the first wavelength of the first light.

A microscope of the present invention comprises a first optical member that reflects a part of stimulation light for stimulating an observation target sample, and a part of excitation light which has a same wavelength as the stimulation light and is for generating fluorescence from the sample, and transmits the part of stimulation light and the part of excitation light, whereby the stimulation light and the excitation light which have entered from different directions are combined and are irradiated onto the sample, and approximately all the fluorescence generated by the irradiation of the excitation light onto the sample is reflected or transmitted.

According to the present invention, brighter and sharper images can be acquired when fluorescent observation is performed while stimulating the sample with light.

BRIEF DESCRIPTION OF THE DRAWINGS

FIG. 2A shows an example of a layer configuration of a dichroic mirror;
FIG. 2B shows an example of a layer configuration of a dichroic mirror;
FIG. 2C shows an example of a layer configuration of a dichroic mirror;
FIG. 4A shows an example of a layer configuration of a dichroic mirror;
FIG. 4B shows an example of a layer configuration of a dichroic mirror;
FIG. 4C shows an example of a layer configuration of a dichroic mirror;
FIG. 6A shows an example of a layer configuration of a dichroic mirror;
FIG. 6B shows an example of a layer configuration of a dichroic mirror;
FIG. 6C shows an example of a layer configuration of a dichroic mirror.

BEST MODE FOR CARRYING OUT THE INVENTION

Figure 1:
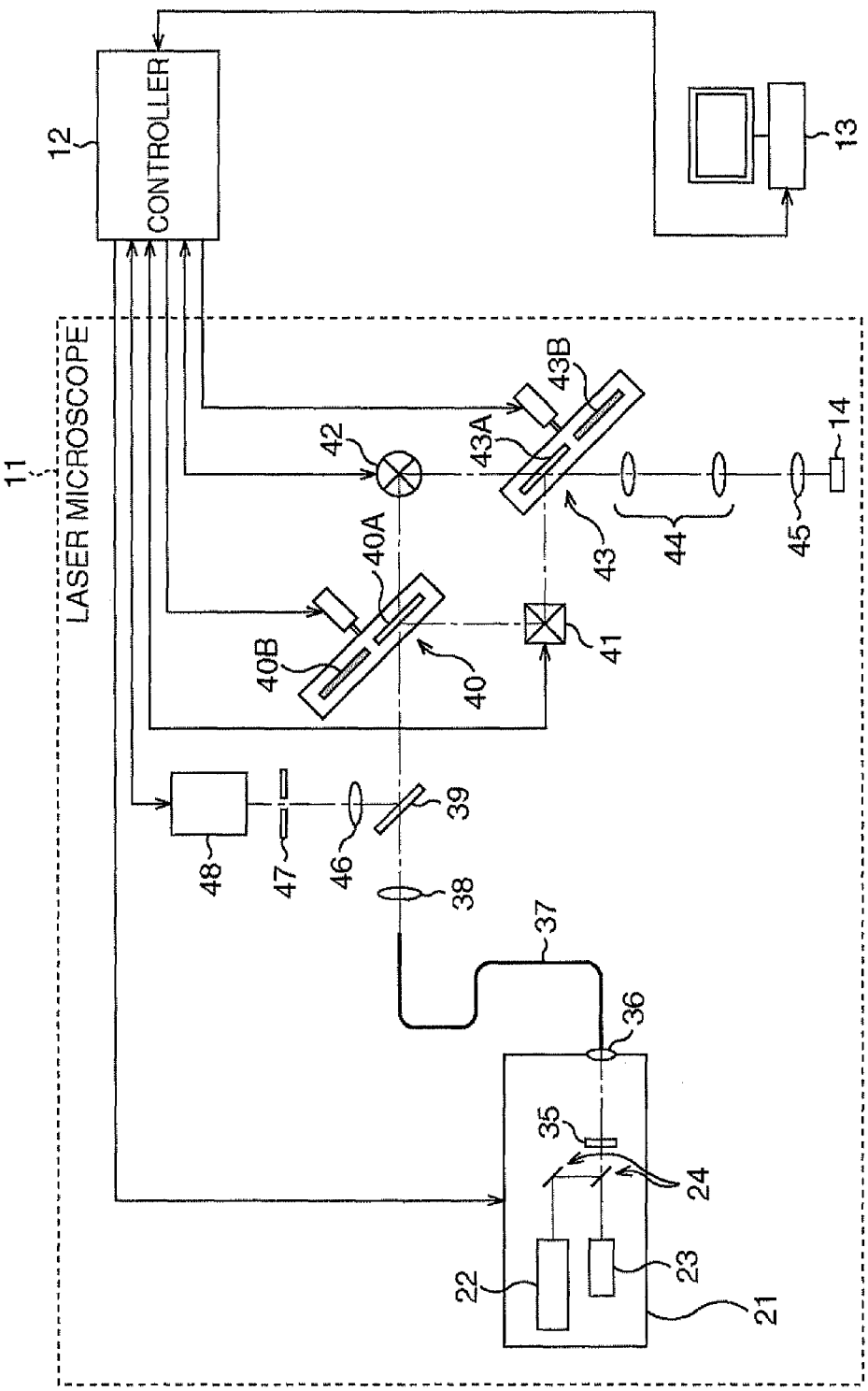
FIG. 1 is a diagram depicting a configuration example of an embodiment of a microscope system to which the present invention is applied.

Embodiments of the present invention will now be described with reference to the drawings.
[Configuration of Microscope System]
FIG. 1 is a diagram depicting a configuration example of an embodiment of a microscope system to which the present invention is applied.

The microscope system comprises a scanning type laser microscope 11 that performs fluorescent observation while stimulating a sample with light, a controller 12 that controls each component of the laser microscope 11, and a computer 13.

An observation target sample 14 is placed on a stage (not illustrated) of the laser microscope 11, and an illumination light emitted from a laser unit 21 is irradiated onto the sample 14.

Two laser light sources 22 and 23 are installed in the laser unit 21, and the illumination light emitted from the laser light source 22 and that emitted from the laser light source 23 are combined on a sample optical path by a combiner mirror 24 which is constituted by a total reflection mirror and a half-mirror. For the illumination light combined by the combiner mirror 24, wavelength selection and intensity modulation are performed by an acousto-optical filter 35 if necessary, and is guided to an optical fiber 37 by a fiber coupler 36.

The illumination light that entered from the laser unit 21 to the optical fiber 37 enters a collimator lens 38 via the optical fiber 37, is collimated into a parallel beam by the collimator lens 38, and enters a dichroic mirror 39.

The illumination light that entered the dichroic mirror 39 transmits through the dichroic mirror 39 and enters an optical path selection unit 40. This dichroic mirror 39 has optical characteristics to transmit light of the illumination light that has a wavelength band to be stimulation light and excitation light, and to reflect light in a wavelength band of fluorescence that is generated in the sample 14.

An optical path selection unit 40 is disposed on an optical path of an illumination light, and selects the optical path of the entered light. In other words, the optical path selection unit 40 is constituted by a turret which is rotationally driven by a motor, and optical members which are disposed on the optical path of the illumination light and are held by the turret.

The turret of the optical selection unit 40 holds a dichroic mirror 40A, which functions as a half-mirror for light having the wavelength band of the illumination light and as a mirror for light having the wavelength band of fluorescence, and a mirror 40B as optical members (deflection elements). The illumination light that entered the optical path selection unit 40 is guided to a scanning unit 41 or a scanning unit 42 depending on the wavelength of the light and the optical member disposed on the optical path of the light.

This dichroic mirror 40A has optical characteristics to transmit approximately half of the entered illumination light, and to reflect the remaining half of the illumination light. In the case of FIG. 1, the dichroic mirror 40A is disposed on the optical path of the illumination light, so approximately half of the illumination light that entered from the dichroic mirror 39 to the dichroic mirror 40A is reflected by the dichroic mirror 40A, and enters the scanning unit 41. The remaining half of the illumination light that entered from the dichroic mirror 39 to the dichroic mirror 40A transmits through the dichroic mirror 40A, and enters the scanning unit 42.

In the laser microscope 11, the illumination light that entered from the dichroic mirror 40A to the scanning unit 41 becomes the excitation light, and the illumination light that entered from the dichroic mirror 40A to the scanning unit 42 becomes the illumination light.

The illumination light (stimulation light) which entered the scanning unit 42 is deflected (reflected) by the scanning unit 42, and enters an optical path selection unit 43. The scanning unit 42 scans the sample 14 with the stimulation light by deflecting the stimulation light, and changing the irradiation position of the stimulation light on the sample 14 in the crosswise direction and the depth direction of FIG. 1. For example, the scanning unit 42 is constituted by two Galvano scanners, and can more freely set a scanning area compared with the scanning unit 41.

The illumination light (excitation light) which entered the scanning unit 41, on the other hand, is deflected (reflected) by the scanning unit 41, and enters the optical path selection unit 43. The scanning unit 41 scans the sample 14 with the excitation light by deflecting the excitation light, and changing the irradation position of the excitation light on the sample 14 in the crosswise direction and the depth direction of FIG. 1. For example, the scanning unit 41 is constituted by two Galvano scanners, and can perform scanning faster than the scanning unit 42.

The optical path selection unit 43 has a same configuration as the optical path selection unit 40, and the optical path selection unit 43 holds a dichroic mirror 43A and a mirror 43B. This dichroic mirror 43A has same optical characteristics as the dichroic mirror 40A, and splits the light having the wavelength band of the illumination light at a predetermined ratio, and reflects almost all light having the wavelength band of fluorescence.

In the case of FIG. 1, the dichroic mirror 43A is disposed on the optical paths of the stimulation light and the excitation light, so a part of the stimulation light which entered the optical path selection unit 43 transmits through the dichroic mirror 43A and is irradiated onto the sample 14 via the relay lens 44 and an object lens 45.

A part of the excitation light which entered the optical path selection unit 43 is reflected by the dichroic mirror 43A, and is irradiated onto the sample 14 via the relay lens 44 and the object lens 45.

Thereby the sample 14 is stimulated by the stimulation light and is also imaged by the excitation light. If the excitation light is irradiated onto the sample 14, fluorescence is generated from the sample 14, and the fluorescence is reflected by the dichroic mirror 43A of the optical path selection unit 43 via the object lens 45 and the relay lens 44, and is descanned by the scanning unit 41.

The descanned fluorescence is reflected by the dichroic mirror 40A, and is further reflected by the dichroic mirror 39, and is condensed by a condensing lens 46. The fluorescence condensed by the condensing lens 46 enters a photodetector 48 via a pin hole 47, and is received. The pin hole 47 is disposed in a focal position of the object lens 45, that is in a position conjugate with the observation surface of the sample 14, so that only fluorescence condensed in a position of the pin hole 47 enters the photodetector 48.

The photodetector 48 receives the entered fluorescence and performs photoelectric conversion, so as to convert the fluorescence into an electric signal that indicates light intensity of the received fluorescence. The electric signal acquired by the photoelectric conversion is supplied from the photodetector 48 to the controller 12. Based on the electric signal supplied from the photodetector 48, the controller 12 generates an observation image which is an image of the observation surface of the sample 14, and supplies the image to the computer 13. The computer 13 displays the observation image supplied from the controller 12 on the display.

Besides the dichroic mirror and the mirror, the turret of the optical path selection unit 40 or the optical path selection unit 43 may hold optical members which directly transmit light, such as a hollow block, a double-sided mirror and a blank glass.

[Configuration Example 1 of Deflection Element]

A concrete configuration example of the dichroic mirror 40A and the dichroic mirror 43A in FIG. 1 will now be described.

A case of observing the sample 14 by fluorescence based on the method called FLIP (Fluorescence Loss In Photobleaching) or FRAP (Fluorescence Recovery After Photobleaching) using CFP (Cyan Fluorescent Protein) will be considered. In this case, wavelength of the stimulation light and that of the excitation light are both 440 nm, and the fluorescence is light having a wavelength band including 510 nm, which is the peak wavelength.

In this example, the dichroic mirror 40A is an optical member created by forming a layered deposited film on a glass substrate, that is, by alternately depositing lithium niobate ($Nb_2O_5$) and silicon dioxide ($SiO_2$) on a glass substrate, as shown in FIG. 2A, FIG. 2B, and FIG. 2C.

In FIG. 2A, FIG. 2B, and FIG. 2C, the column "Layer Number" indicates a layer number that specifies the position of the layer of a substance deposited on the glass substrate. The column "Substance" indicates a substance constituting a layer specified by the layer number, and the column "Film Thickness (nm)" indicates thickness (film thickness) of the layer specified by the layer number.

In FIG. 2A, FIG. 2B, and FIG. 2C, the layer number of each layer is assigned such that the layer number of the layer becomes smaller as the layer becomes closer to the surface of the glass substrate. For example, the layer of which layer number is "1" is a layer (film) formed by depositing lithium niobate on the surface of the glass substrate, and the thickness of the layer is 37.33 nm. The layer of which layer number is "2" is a layer formed by depositing silicon dioxide on the surface of the layer of which layer number is "1", so that the film thickness becomes 10 nm.

In this example, the dichroic mirror 40A is created by forming 176 layers of films on the glass substrate. The dichroic mirror 40A having this configuration has the optical characteristics shown in FIG. 3.

Figure 3:
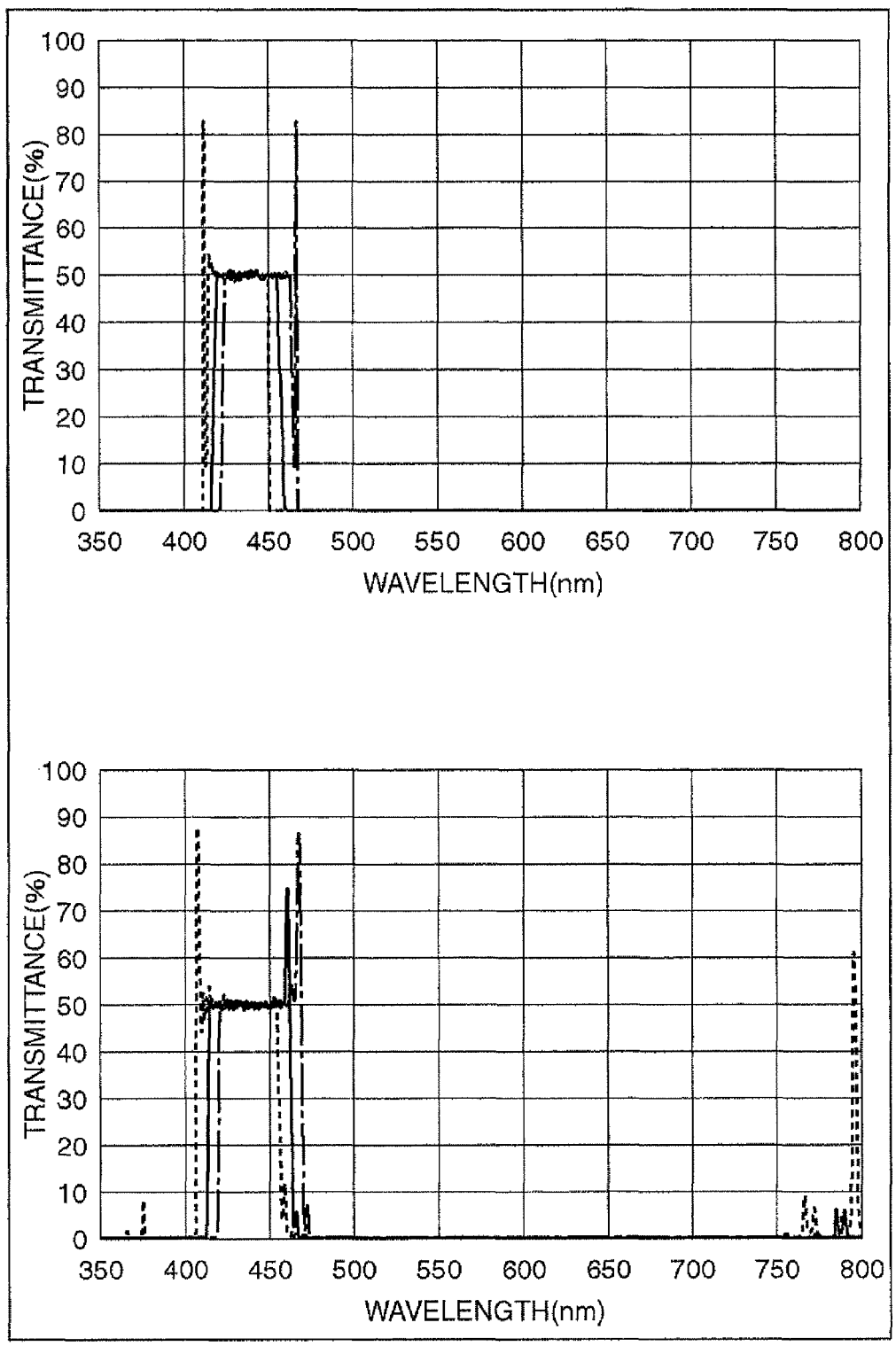
FIG. 3 shows an optical characteristic example of a dichroic mirror.

In FIG. 3, the ordinate is the transmittance of light that entered the dichroic mirror 40A, and the abscissa is the wavelength of the light. The top graph in FIG. 3 shows the optical characteristics of the S-polarized light that entered the dichroic mirror 40A, and the bottom graph in FIG. 3 shows the optical characteristics of the P-polarized light that entered the dichroic mirror 40A.

In both the top and bottom graphs in FIG. 3, the solid line, the dotted line and the dashed line indicate the optical characteristics of the light when the incident angle to the dichroic mirror 40A is 45°, 52° and 38° respectively. The incident angle here means an angle formed by a line that is normal to the surface (reflection surface) of the dichroic mirror 40A and the optical path of the light.

In the case of FIG. 3, the transmittance of light of which wavelength is 420 nm to 450 nm is approximately 50%, and the transmittance of light having the other wavelength is approximately 0%. Therefore if an illumination light of which wavelength is 440 nm enters the dichroic mirror 40A, about half of the illumination light transmits through the dichroic mirror 40A, and the remaining half of the illumination light is reflected by the dichroic mirror 40A. On the other hand, fluorescence of which wavelength is about 476 nm is almost all reflected by the dichroic mirror 40A.

In this example, the dichroic mirror 43A has the same optical characteristics as the dichroic mirror 40A. In other words, the dichroic mirror 43A is an optical member that has the layer configuration shown in FIG. 2A, FIG. 2B, and FIG. 2C, and has the optical characteristics shown in FIG. 3.

If the dichroic mirror 40A or the dichroic mirror 43A, which transmits light having a predetermined wavelength band at a predetermined transmittance and reflects almost all the light having other wavelength bands, is disposed on the optical path of the laser microscope 11, then a drop in light quantity of the fluorescence can be controlled. As a consequence, brighter and sharper observation images can be acquired even when fluorescent observation is performed while stimulating the sample with stimulation light having the same wavelength as the excitation light.

[Operation of Microscope System]

Now an operation of the microscope system when the dichroic mirror 40A and the dichroic mirror 43A are constructed as described with reference to FIG. 2A, FIG. 2B, FIG. 2C, and FIG. 3 will be described.

If the user operates the computer 13 and instructs to start observing the sample 14, the controller 12 operates the optical path selection unit 40 and the optical path selection unit 43 according to the instruction of the computer 13. The optical path selection unit 40 rotates the turret based on the control by the controller 12, and disposes the dichroic mirror 40A on the optical path of the illumination light. The optical path selection unit 43 rotates the turret based on the control by the controller 12, and disposes the dichroic mirror 43A on the optical path of the illumination light (stimulation light or excitation light).

The controller 12 allows the laser unit 21 to emit the illumination light of which wavelength is 440 nm, and controls the acousto-optical filter 35 to adjust light quantity of the illumination light. The illumination light emitted from the laser unit 21 enters the dichroic mirror 40A via the optical fiber 37 to the dichroic mirror 39.

The illumination light that entered the dichroic mirror 40A is split into the excitation light and the stimulation light by reflection or transmission in the dichroic mirror 40A.

In other words, the illumination light that transmitted through the dichroic mirror 40A becomes the stimulation light, and is irradiated onto the sample 14 via the scanning unit 42 to the object lens 45. In this case, the scanning unit 42 deflects the stimulation light so as to scan the sample 14 with the stimulation light.

The illumination light reflected by the dichroic mirror 40A, on the other hand, becomes the excitation light and is irradiated onto the sample 14 via the scanning unit 41, and the dichroic mirror 43A to the object lens 45. In this case, the scanning unit 41 deflects the excitation light so as to scan the sample 14 with the excitation light.

In this microscope system, the stimulation light and the excitation light can be scanned using the different scanning units, hence a desired area of the sample 14 is stimulated, and at the same time the excitation light can be irradiated onto an area that is different from the area receiving stimulation. Since the laser beam need not be wastefully irradiated onto the entire sample 14 when the stimulation light is irradiated onto a specific area of the sample 14, discoloration of the sample 14 can be prevented.

If the excitation light is irradiated onto the sample 14 in this way, the fluorescence is generated from the sample 14, and this fluorescence is reflected by the dichroic mirror 43A via the object lens 45 and the relay lens 44, and is descanned by the scanning unit 41. The fluorescence emitted from the scanning unit 41 is reflected by the dichroic mirror 40A, and is received by the photodetector 48 via the dichroic mirror 39 to the pin hole 47.

If the fluorescence is photoelectric-converted by the photodetector 48, an electric signal, corresponding to the light quantity of the received fluorescence, is supplied from the photodetector 48 to the controller 12, so the controller 12 generates an observation image from this electric signal, and supplies the image to the computer 13. Thereby the user can observe the sample 14 by viewing the observation image displayed on the computer 13.

By using the dichroic mirror 40A and the dichroic mirror 43A, which reflect almost all the fluorescence as the optical member that splits the illumination light into the stimulation light and the excitation light, and as the optical member that combines the stimulation light and the excitation light in this way, a drop in light quantity of the fluorescence can be controlled. As a consequence, brighter and sharper observation images can be acquired by sufficiently conserving the light quantity of the fluorescence.

In the above description, the dichroic mirror 40A and the dichroic mirror 43A reflect almost all the fluorescence, but to be more specific, it is sufficient if the reflectance of the fluorescence of these dichroic mirrors is 80% or more. Similarly, a description indicating that the dichroic mirror 40A and the dichroic mirror 43A transmit almost all the light can be interpreted that 80% or more of the light is transmitted would be more specific.

[Configuration Example 2 of Deflection Element]

Another concrete configuration example of the dichroic mirror 40A and the dichroic mirror 43A will now be described. Here a case of observing the sample 14 using fluorescence based on a DRONPA-Green method will be described.

In this case, light of which wavelength is 405 nm and light of which wavelength is 488 nm are used as the stimulation light, and light of which wavelength is 488 nm is used as the excitation light. The fluorescence is light having a wavelength band including 510 nm, which is the peak wavelength.

In this example, the dichroic mirror 40A is an optical member created by alternately depositing lithium niobate and silicon dioxide on a glass substrate, as shown in FIG. 4A, FIG. 4B, and FIG. 4C.

Each "Layer Number", "Substance" and "Film Thickness (nm)" column in FIG. 4A, FIG. 4B, and FIG. 4C is the same as the case of FIG. 2A, FIG. 2B, and FIG. 2C, therefore redundant description thereof is omitted. In FIG. 4A, FIG. 4B, and FIG. 4C as well, the layer number of each layer is assigned such that the layer number of the layer becomes smaller as the layer becomes closer to the surface of the glass substrate.

In the example of FIG. 4A, FIG. 4B, and FIG. 4C, the dichroic mirror 40A is constituted by 105 layers, which are formed by alternately depositing lithium niobate and silicon dioxide. The dichroic mirror 40A having this configuration has the optical characteristics shown in FIG. 5.

Figure 5:
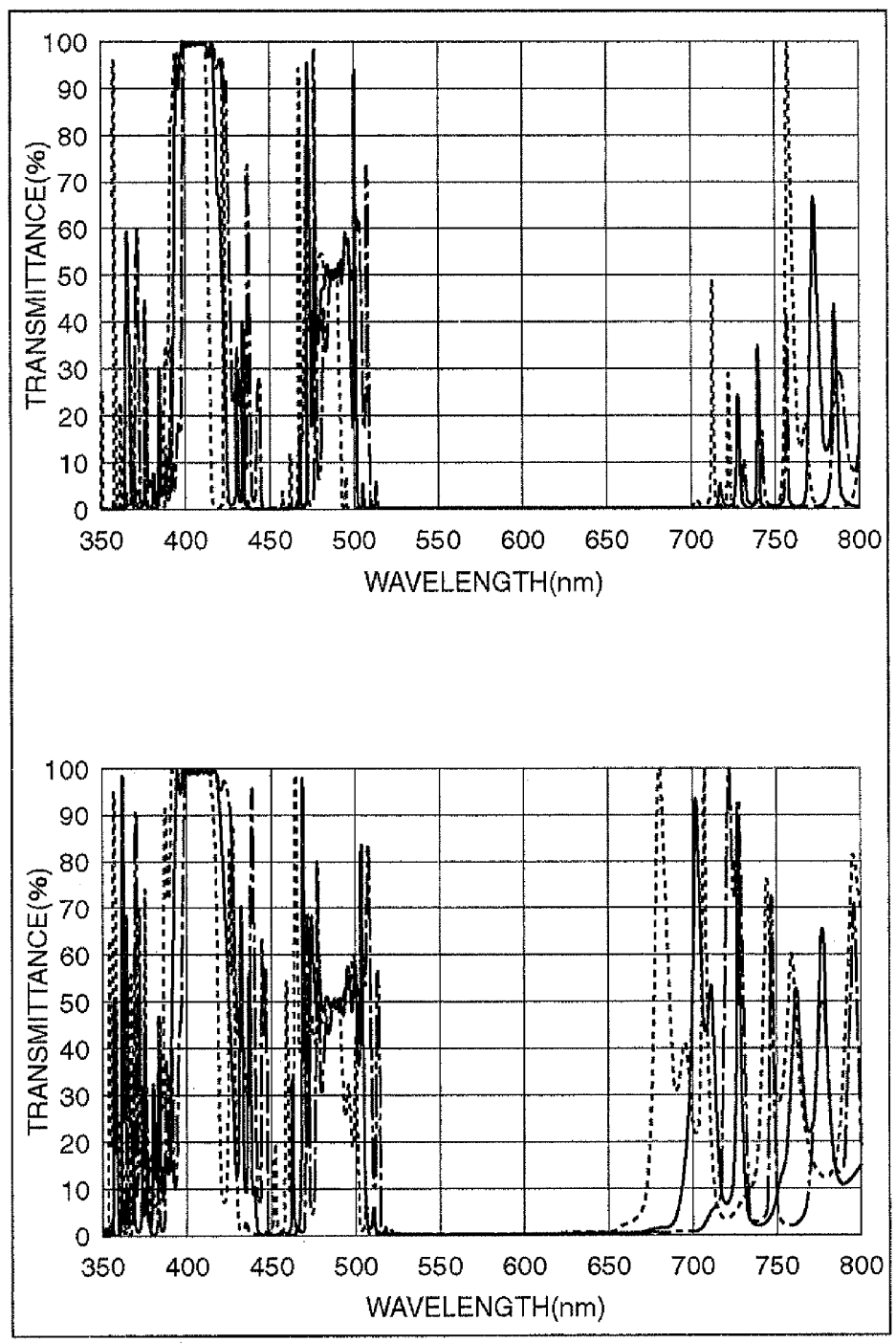
FIG. 5 shows an optical characteristic example of a dichroic mirror.

In FIG. 5, the ordinate is the transmittance of light that entered the dichroic mirror 40A, and the abscissa is the wavelength of the light. The top graph in FIG. 5 shows the optical characteristics of the S-polarized light that entered the dichroic mirror 40A, and the bottom graph in FIG. 5 shows the optical characteristics of the P-polarized light that entered the dichroic mirror 40A. In both the top and bottom graphs in FIG. 5, the solid line, the dotted line and the dashed line indicate the optical characteristics of the light of which incident angle to the dichroic mirror 40A is 45°, 52° and 38° respectively.

In the case of FIG. 5, the transmittance of light of which wavelength is 400 nm to 420 nm is approximately 100%, and the transmittance of light of which wavelength is 470 nm to 500 nm is approximately 50%. The transmittance of light of which wavelength is 500 nm to 670 nm is approximately 0%.

Therefore if illumination light constituted by light of which wavelength is 405 nm and light of which wavelength is 488 nm enters the dichroic mirror 40A, almost all the light of which wavelength is 405 nm and almost half of the light of which wavelength 488 nm transmit through the dichroic mirror 40A, and become the stimulation light. Almost half of the light of which wavelength is 488 nm is reflected by the dichroic mirror 40A, and becomes the excitation light.

The dichroic mirror 43A has the same layer configuration and the same optical characteristics as the dichroic mirror 40A. Therefore almost all the light of which wavelength is 405 nm and almost half of the light of which wavelength is 488 nm, out of the stimulation light, transmit through the dichroic mirror 43A, and are irradiated onto the sample 14. Almost half of the light of which wavelength is 488 nm, out of the excitation light, is reflected by the dichroic mirror 43A, and is irradiated onto the sample 14.

The fluorescence of which wavelength is about 510 nm generated in the sample 14, on the other hand, is almost all reflected by the dichroic mirror 43A and the dichroic mirror 40A, and is received by the photodetector 48.

In this configuration of the dichroic mirror 43A and the dichroic mirror 40A as well, a drop in light quantity of the fluorescence can be controlled, and brighter and sharper observation images can be acquired.

[Configuration Example 3 of Deflection Element]

Another concrete configuration example of the dichroic mirror 40A and the dichroic mirror 43A will now be described. In this example as well, a case of observing the sample 14 using fluorescence based on a DRONPA-Green method will be described.

In this case as well, light of which wavelength is 405 nm and light of which wavelength is 488 nm are used as the stimulation light, and light of which wavelength is 488 nm is used as the excitation light. The fluorescence is light having a wavelength band including 510 nm, which is the peak wavelength.

In this example, the dichroic mirror 40A is an optical member created by alternately depositing lithium niobate and silicon dioxide on the glass substrate, as shown in FIG. 6A, FIG. 6B, and FIG. 6C. Each "Layer Number", "Substance" and "Film Thickness (nm)" column in FIG. 6A, FIG. 6B, and FIG. 6C are the same as the case of FIG. 2A, FIG. 2B, and FIG. 2C, therefore redundant description thereof is omitted. In FIG. 6A, FIG. 6B, and FIG. 6C as well, the layer number of each layer is assigned such that the layer number of the layer becomes smaller as the layer becomes closer to the surface of the glass substrate.

In the example in FIG. 6A, FIG. 6B, and FIG. 6C, the dichroic mirror 40A is constituted by 185 layers, which are formed by alternately depositing lithium niobate and silicon dioxide. The dichroic mirror 40A having this configuration has the optical characteristics shown in FIG. 7.

Figure 7:
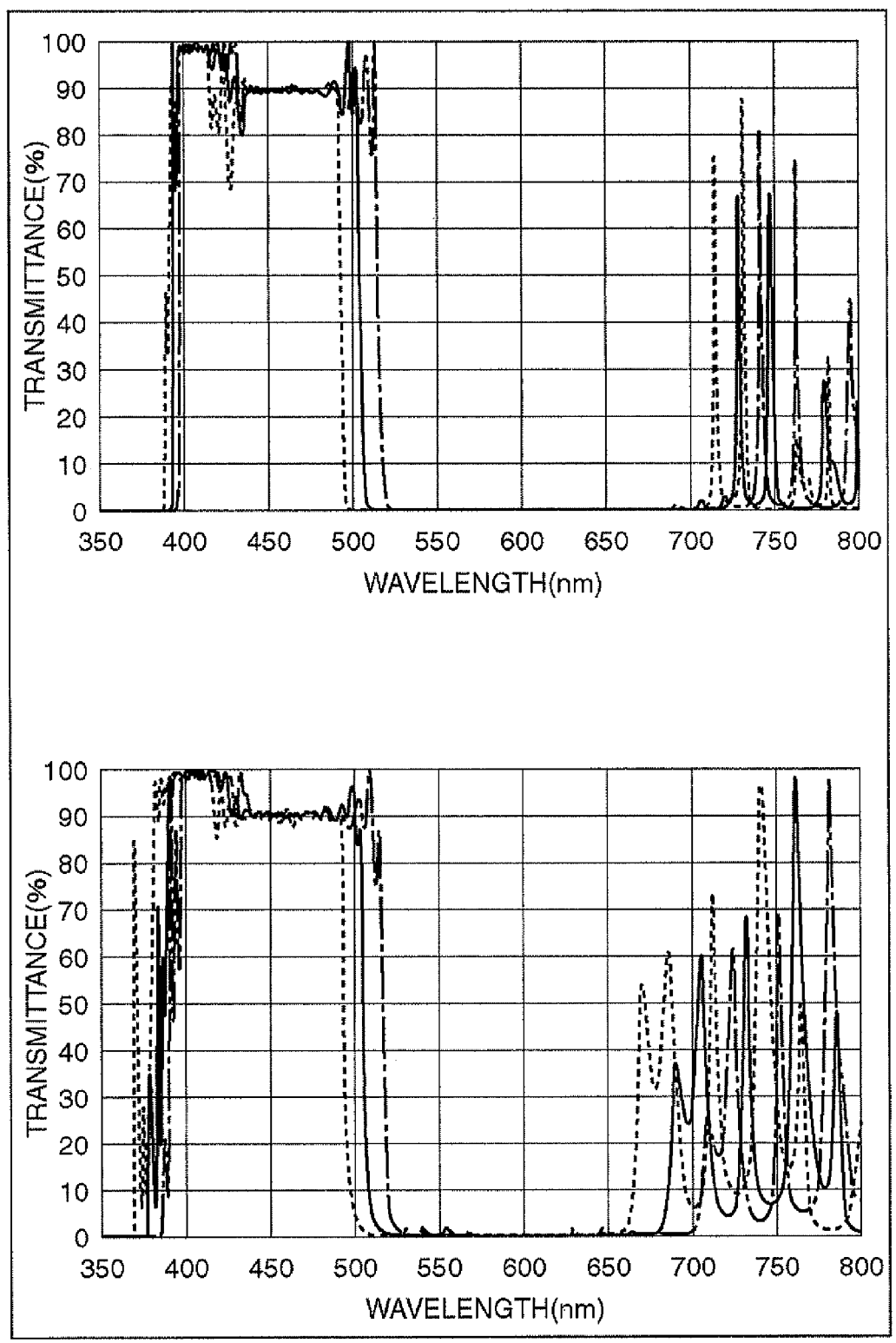
FIG. 7 shows an optical characteristic example of a dichroic mirror.

In FIG. 7, the ordinate is the transmittance of the light that entered the dichroic mirror 40A, and the abscissa is the wavelength of the light. The top graph in FIG. 7 shows the optical characteristics of the S-polarized light that entered the dichroic mirror 40A, and the bottom graph in FIG. 7 shows the optical characteristics of the P-polarized light that entered the dichroic mirror 40A. In both the top and bottom graphs in FIG. 7, the solid line, the dotted line and the dashed line indicate the optical characteristics of the light of which incident angle to the dichroic mirror 40A is 45°, 52° and 38° respectively.

In the case of FIG. 7, the transmittance of light of which wavelength is 400 nm to 430 nm is approximately 100%, and the transmittance of light of which wavelength is 430 nm to 500 nm is approximately 90%. In other words, the ratio of transmission and reflection of the light of which wavelength band is 430 nm to 500 nm is 9:1. The transmittance of light of which wavelength is 510 nm to 660 nm is approximately 0%.

Therefore if illumination light constituted by light of which wavelength is 405 nm and light of which wavelength is 488 nm enters the dichroic mirror 40A, almost all the light of which wavelength is 405 nm and almost 90% of the light of which wavelength is 488 nm transmit through the dichroic mirror 40A, and become the stimulation light. Almost 10% of the light of which wavelength is 488 nm is reflected by the dichroic mirror 40A, and becomes the excitation light.

The dichroic mirror 43A has the same layer configuration and the same optical characteristics as the dichroic mirror 40A. Therefore almost all the light of which wavelength is 405 nm, and almost 90% of the light of which wavelength is 488 nm, out of the stimulation light, transmit through the dichroic mirror 43A, and are irradiated onto the sample 14. Almost 10% of the light of which wavelength is 488 nm, out of the excitation light, is reflected by the dichroic mirror 43A, and is irradiated onto the sample 14.

The fluorescence of which wavelength is about 510 nm generated in the sample 14, on the other hand, is almost all reflected by the dichroic mirror 43A and the dichroic mirror 40A, and is received by the photodetector 48.

In this configuration of the dichroic mirror 43A and the dichroic mirror 40A as well, a drop in the light quantity of the fluorescence can be controlled, and brighter and sharper observation images can be acquired.

In the dichroic mirror 40A and the dichroic mirror 43A, if the ratio of transmission and reflection of the light of which wavelength is 488 nm, to be the stimulation light and the excitation light, has already been set to an appropriate value, like the case of this example, then it is unnecessary to adjust the light quantity of the stimulation light and the excitation light using an acousto-optic filter or the like.

In the above example, the illumination light reflected by the dichroic mirror 40A and the dichroic mirror 43A is used as the excitation light, but the illumination light transmitted through these dichroic mirrors may be used as the excitation light.

In such a case, the light transmitted through the dichroic mirror 40A and the dichroic mirror 43A, out of the illumination light, is used as the excitation light, and the light reflected by the dichroic mirror 40A and the dichroic mirror 43A is used as the stimulation light. In this case, the dichroic mirror 40A and the dichroic mirror 43A have optical characteristics to transmit almost all the fluorescence generated from the sample 14.

In the above description, the dichroic mirror 40A and the dichroic mirror 43A are disposed on the optical path of the laser microscope 11 which functions as a confocal microscope, but the present invention can be applied not only to a confocal microscope, but also to a microscope for observing the sample 14 with fluorescence while stimulating the sample 14 with light.

For example, the microscope may be configured such that the stimulation light and the excitation light, which are emitted from different light sources and have a same wavelength, are combined by the dichroic mirror 43A and are irradiated onto the sample 14, and almost all the fluorescence from the sample 14 is reflected by or is transmitted through the dichroic mirror 43A. In this microscope, it is not always required to scan the sample 14 using the stimulation light or the excitation light, and if scanning is performed, this microscope functions as a confocal microscope (scanning microscope).

Embodiments of the present invention are not limited to the above mentioned embodiments, but numerous modifications can be made without departing from the true spirit and scope of the invention.

EXPLANATION OF REFERENCE NUMERALS

11 laser microscope
12 controller
13 computer
14 sample
21 laser unit
40 optical path selection unit
40A dichroic mirror
41 scanning unit
42 scanning unit
43 optical path selection unit
43A dichroic mirror
45 object lens

The invention claimed is:

1. A microscope comprising:
a first optical member configured to receive a first light having a first wavelength included in a first wavelength region and to separate the first light into stimulation light and excitation light by transmitting and reflecting the first light based on a first predetermined ratio:
a first scanning unit configured to scan a sample with the stimulation light by receiving and deflecting the stimulation light;
a second scanning unit configured to scan the sample with the excitation light by receiving and deflecting the excitation light; and
a second optical member configured to receive the stimulation light from the first scanning unit and the excitation light from the second scanning unit and to guide both the stimulation light and the excitation light to an objective lens to irradiate the sample by transmitting and reflecting the stimulation light and the excitation light based on a second predetermined ratio for the stimulation light and a third predetermined ratio for the excitation light, and to reflect or transmit approximately all fluorescence generated from the irradiated sample, which has a wavelength included in a second wavelength region.

2. The microscope according to claim 1, wherein the first optical member reflects or transmits approximately all of the fluorescence from the sample that enters the first optical member via the second optical member and the second scanning unit.

3. The microscope according to claim 1, wherein the first optical member and the second optical member transmit approximately half of the light of the first wavelength region and reflect approximately half of the light of the first wavelength region.

4. The microscope according to claim 1, wherein the first optical member and the second optical member are further configured to transmit or reflect approximately all light of a third wavelength region, and the first optical member is configured to receive a second light having a second wavelength included in the third wavelength region and transmit or reflect approximately all the second light as the stimulation light.

5. The microscope according to claim 1, wherein the second optical member is configured to reflect or transmit the fluorescence to a same side of the second optical member as the side which the excitation light is irradiated toward the second optical member.

6. The microscope according to claim 1, wherein the second scanning unit is configured to deflect the fluorescence transmitted through or reflected by the second optical member.

7. The microscope according to claim 1, wherein while the stimulation light is irradiated onto a desired area of the sample by controlling the first scanning unit, the excitation light is irradiated onto an area that is different from the desired area by controlling the second scanning unit.

8. The microscope according to claim 1, wherein the wavelength of the fluorescence includes a part of a range of approximately 510 nm to 670 nm.

9. The microscope according to claim 1, wherein the second optical member is obtained by forming a first substance and a second substance alternately on a substrate.

* * * * *